United States Patent [19]

Clark et al.

[11] Patent Number: 5,476,995
[45] Date of Patent: * Dec. 19, 1995

[54] PEPTIDE PRODUCTION

[75] Inventors: Anthony J. Clark, Edinburgh, Scotland; Richard Lathe, Strasbourg, France

[73] Assignee: PPL Therapeutics (Scotland) Ltd., Edinburg, Scotland

[*] Notice: The portion of the term of this patent subsequent to Jun. 21, 2011, has been disclaimed.

[21] Appl. No.: 931,864

[22] Filed: Aug. 18, 1992

Related U.S. Application Data

[63] Continuation of Ser. No. 796,917, Nov. 22, 1991, Pat. No. 5,322,755, which is a continuation of Ser. No. 165,988, Apr. 29, 1988, abandoned.

[30] Foreign Application Priority Data

Jun. 30, 1986 [GB] United Kingdom .................. 8615942

[51] Int. Cl.$^6$ ..................................... C12N 15/00
[52] U.S. Cl. ............... 800/2; 800/DIG. 1; 435/69.1; 435/172.3; 435/317.1; 435/320.1; 935/11; 935/111
[58] Field of Search ................... 800/2, DIG. 1; 435/172.3, 69.1, 317.1; 935/11, 111

[56] References Cited

U.S. PATENT DOCUMENTS

| | | | |
|---|---|---|---|
| 4,736,866 | 4/1988 | Leder et al. | 800/1 |
| 4,870,009 | 9/1989 | Evans et al. | 435/70 |
| 4,873,316 | 10/1989 | Meade et al. | 530/412 |

FOREIGN PATENT DOCUMENTS

| | | |
|---|---|---|
| 0264166 | 4/1988 | European Pat. Off. . |
| WO82/04443 | 12/1982 | WIPO . |

OTHER PUBLICATIONS

Andres et al., Experientia 42(6): 673 (1986).
Campbell et al., Nucleic Acids Res. 12(22): 8685–8697 (1984).
Richards et al., J. Biol. Chem. 256(1): 526–532 (1981).
Wilmut et al., A revolution in animal breeding, *New Scientist* 7:56–59 (1989).
Wright et al., High Level Expression of Active Human Alpha–1–Antitrypsin in the Milk of Transgenic Sheep, *Bio/Technology* 9:830–834 (1991).
van der Putten et al., Developmental fate of a human insulin gene in a transgenic mouse, *Mol. Gen. Genet.* 198:128–138 (1984).
Wagner et al., Microinjection of a rabbit β–globin gene into zygotes and its subsequent expression in adult mice and their offspring, *Proc. Natl. Acad. Sci. USA* 78:6376–6380 (1981).
Wall et al., High–level synthesis of a heterologous milk protein in the mammary glands of transgenic swine, *Proc. Natl. Acad. Sci. USA* 88:1696–1700 (1991).
Swift et al., Tissue–Specific Expression of the Rat Pancreatic Elastase I Gene in Transgenic Mice, *Cell* 38:639–646 (1984).

Townes et al., Erythroid–specific expression of human β–globin genes in transgenic mice, *The EMBO Journal* 4(7):1715–1723 (1985).
Van Brunt, J., Molecular Farming: Transgenic Animals as Bioreactors, *Bio/Technology* 6(10):1149–1154 (1988).
Palmiter et al., Transgenic Mice, *Cell* 41:343–345 (1985).
Shani, M., Tissue–specific expression of rat myosin light–chain 2 gene in transgenic mice, *Nature* 314:283–286 (1985).
Stewart et al., Spontaneous Mammary Adenocarcinomas in Transgenic Mice That Carry and Express MTV/myc Fusion Genes, *Cell* 38:627–637 (1984).
McKnight et al., Expression of the Chicken Transferrin Gene in Transgenic Mice, *Cell* 34:335–341 (1983).
Mercier et al., Construction and identification of recombinant plasmids carrying cDNAs coding for ovine αs1–, αs2–, β–, k–casein and β–lactoglobulin . . . , *Biochimie* 67:959–971 (1985).
Palmiter et al., Dramatic growth of mice that develop from eggs microinjected with metallothionein growth hormone fusion genes, *Nature* 300:611–615 (1982).
Krumlauf et al., Developmental Regulation of β–Fetoprotein Genes in Transgenic Mice, *Molecular and Cellular Biology* 5(7):1639–1648 (1985).
Lacy et al., A Foreign β–Globin Gene in Transgenic Mice: Integration at Abnormal Chromosomal Positions and Expression in Inappropriate Tissues, *Cell* 34:343–358 (1983).
Magram et al., Developmental regulation of a cloned adult β–globin gene in transgenic mice, *Nature* 315:338–340 (1985).
Hanahan, D., Heritable formation of pancreatic β–cell tumors in transgenic mice expressing recombinant insulin/simian virus 40 oncogenes, *Nature* 315:115–122 (1985).
Hochi et al., Successful Production of Transgenic Rats, *Animal Biotechnology* 1(2):175–184 (1990).
Illmensee et al., Nuclear and Gene Transplantation in the Mouse, *Developmental Biology Using Purified Genes*, Academic Press, Inc., pp. 607–619 (1981).
Gordon et al., Gene Transfer into Mouse Embryos: Production of Transgenic Mice by Pronuclear Injection, *Methods in Enzymology* 101:411–433 (1983).
Hammer et al., Production of transgenic rabbits, sheep and pigs by microinjection, *Nature* 315:680–683 (1985).

(List continued on next page.)

*Primary Examiner*—Jasemine C. Chambers
*Attorney, Agent, or Firm*—Sterne, Kessler, Goldstein & Fox

[57] ABSTRACT

A method of producing a proteinaceous compound, involves incorporating a DNA sequence coding for polypeptide into a gene of a mammal (such as a sheep) coding for a milk whey protein in such a way that the DNA sequence is expressed in the mammary gland of the adult female mammal. The proteinaceous compound may be a (optionally modified) protein such as a blood coagulation factor. The DNA sequence is preferably inserted into the first exon of a gene coding for a whey protein such as beta-lactoglobulin. The proteinaceous compound will generally be recovered from milk of the female mammal, but may (for example if it is an enzyme) be used in situ.

4 Claims, 9 Drawing Sheets

OTHER PUBLICATIONS

Hammer et al., Partial correction of murine hereditary growth disorder by germ–line incorporation of a new gene, *Nature* 311:65–67 (1984).

Clark et al., The germline manipulation of livestock: progress during the past five years, *Proceedings of the New Zealand Society of Animal Production* 50:167–180 (1990).

First et al., The Production and Potential Use of Transgenic Livestock, *Proc. 39th Ann. Reciprocal Meat Conf.* 41–46 (1986).

Gordon et al., Genetic transformation of mouse embryos by microinjection of purified DNA, *Proc. Natl. Acad. Sci. USA* 77(12):7380–7384 (1980).

Buhler et al., Rabbit β–Casein Promoter Directs Secretion of Human Interleukin–2 into the Milk of Transgenic Rabbits, *Bio/Technology* 8:140–143 (1990).

Burki et al., Transplantation of the human insulin gene into fertilized mouse eggs, *The EMBO Journal* 1(1):127–131 (1982).

Clark et al., Pharmaceuticals from transgenic livestock, *TIBTECH* 5:20–24 (1987).

Brinster et al., Expression of a microinjected immunoglobulin gene in the spleen of transgenic mice, *Nature* 306:332–336 (1983).

Brinster et al., Somatic Expression of Herpes Thymidine Kinase in Mice following Injection of a Fusion Gene into Eggs, *Cell* 27:223–231 (1981).

Brinster et al., Factors affecting the efficiency of introducing foreign DNA into mice by microinjecting eggs, *Proc. Natl. Acad. Sci. USA* 82:4438–4442 (1985).

Anson et al., The gene structure of human anti–haemophilic factor IX, *The EMBO Journal* 3(5):1053–1060 (1984).

Brem and Weidle, "Production of Proteins with Antibody Activity in Transgenic Mammals", Frontiers of Biotechnology in Agriculture Meetings, 1991 (Abstract).

Brem and Hartl, "High–level Expression of Prochymosin in the Milk of Transgenic Rabbits", Frontiers of Biotechnology in Agriculture Meeting, 1991 (Abstract).

PEPTIDE PRODUCTION

This application is a continuation of application Ser. No. 07/796,917, filed Nov. 22, 1991, now U.S. Pat. No. 5,322, 755. Ser. No. 07/796,917 is a continuation of Ser. No. 07/165,988, filed Apr. 29, 1988, now abandoned.

This invention relates to a method of producing a substance comprising a polypeptide. More particularly, the invention relates to protein production and to the production of biological materials whose formation is catalysed by enzymic proteins.

Recombinant DNA technology has been used increasingly over the past decade for the production of commercially important biological materials. To this end, the DNA sequences encoding a variety of medically important human proteins have been cloned. These include insulin, plasminogen activator, alpha$_1$-antitrypsin and coagulation factors VIII and IX. At present, even with the emergent recombinant DNA techniques, these proteins are usually purified from blood and tissue, an expensive and time consuming process which may carry the risk of transmitting infectious agents such as those causing AIDS and hepatitis.

Although the expression of DNA sequences in bacteria to produce the desired medically important protein looks an attractive proposition, in practice the bacteria often prove unsatisfactory as hosts because in the bacterial cell foreign proteins are unstable and are not processed correctly.

Recognizing this problem, the expression of cloned genes in mammalian tissue culture has been attempted and has in some instances proved a viable strategy. However batch fermentation of animal cells is an expensive and technically demanding process.

There is therefore a need for a high yield, low cost process for the production of biological substances such as correctly modified eukaryotic polypeptides. The absence of agents that are infectious to humans would be an advantage in such a process.

According to a first aspect of the present invention, there is provided a method of producing a substance comprising a polypeptide, the method comprising incorporating a DNA sequence coding for the polypeptide into a gene of a mammal coding for a milk whey protein in such a way that the DNA sequence is expressed in the mammary gland of the adult female mammal. The substance will generally be recovered from milk of the adult female mammal, either before or preferably after post-translational modification.

As used in this specification, the term "polypeptide" refers to a molecule comprising a chain of amino acids, whether sufficiently long or not to be properly classed as a protein. The polypeptide is preferably sufficiently long to be a protein. The "substance comprising a polypeptide" may be the polypeptide itself, or it may be a modified (for example, glycosylated) polypeptide. Alternatively, or in addition, the substance can be cross linked, by post-translational modification of a polypeptide.

The present invention may be used to produce, for example, peptide hormones, blood coagulation factors (particularly factors VIII and IX) or subunits of them (particularly factors VIII and IX), blood proteins (for example beta-globin) and serum proteins (for example alpha$_1$-antitrypsin) proteins for foodstuffs, including natural or altered milk proteins of the host mammal, or enzymes.

Enzymes produced by the present invention may be able to act on their substrates in situ in the mammary gland, and so it can be seen that the present invention encompasses a method of producing a substance which is the reaction product of an enzyme, the method comprising incorporating a DNA sequence coding for the enzyme into a gene of a mammal coding for a milk whey protein in such a way that the DNA sequence is expressed in the mammary gland of the adult female mammal, whereafter it catalyses the formation of the reaction product from one or more substrates of the enzyme. The reaction product will generally be recovered from milk of the adult female mammal.

The DNA sequence coding for the peptide ("the DNA sequence of interest") is preferably incorporated in vitro into a milk whey protein gene which is expressible in the mammary gland of an adult female mammal to form a fusion gene and the fusion gene is incorporated into the germline by injection into a fertilized egg of the mammal, whereafter the injected fertilized egg is allowed to develop into an adult female mammal. It is to be expected that not all the injected eggs will develop into adult females expressing the DNA sequence of interest. Apart from anything else approximately half the animals will be male, from which females can be bred in the following generations.

The relevant techniques whereby foreign DNA sequences can be introduced into the mammalian germ line have been developed in the mouse. At present the most efficient route entails the direct microinjection of a few hundred linear molecules of DNA into a pro-nucleus of a fertilized one cell egg, and this is the method of preference in the present invention. Microinjected eggs may then subsequently be transferred into the oviducts of pseudopregnant foster mothers and allowed to develop. It has been reported by Brinster et al in *Proc Natl Acad Sci* 82 (1985) 4438–4442 that about 25% of the mice that develop inherit one or more copies of the microinjected DNA. From a commercial point of view, it is clearly preferable to use as the host mammal in the present invention a species that is likely to have a larger milk yield. For this reason, domestic livestock animals such as sheep, pigs and cattle are preferred, as will be discussed in more detail below.

Working with large domestic animals requires a considerable investment, particularly in the number of animals required and their cost. While it is normal to obtain up to 30 eggs per superovulated mouse, a ewe gives only three to five. A further problem encountered with farm animals is that the eggs are opaque due to the presence of numerous vesicles, and this makes the identification and successful injection of pronuclei more difficult. Nevertheless, microinjection of DNA into eggs of rabbits, sheep and pigs has been reported by Hammer et al, *Nature* 315 (1985) 680–683, who inserted a metallothionein-growth hormone fusion gene into the germ line of all three mammals.

In the pig, 2,035 eggs were injected and transferred; 192 piglets were born, of which 20 carried the fusion gene. The results were not so encouraging in sheep; 1,032 eggs were injected and transferred, but 73 lambs were born of which only one contained the foreign DNA sequence.

Once integrated into the germ line, the foreign DNA may be expressed in the tissue of choice at high levels to produce a functional protein which can readily be harvested from the animal. To accomplish this, the DNA sequence coding for the peptide of interest will generally be fused to a DNA sequence or sequences that will mediate its expression in a suitable tissue. Although some initial experiments in mice show that tissue specific expression of inserted DNA to be somewhat variable (for example, Lacey et al, *Cell* 34 (1983) 343–356), the general concensus now is that correct tissue specific expression of most transfected genes is achievable. See Brinster et al *Cell* 27 (1981) 223–231; Swift et al *Cell* 38 (1984) 639–646; Shani *Nature* 314 (1985) 283–286; and Magram et al *Nature* 315 (1985) 338–340. For correct tissue specificity, it does appear to be important to remove all the prokaryote vector sequences, which are used in the cloning of DNA sequence of interest, prior to microinjection (Krumlauf et al *Mol. Cell Biol.* 5 (1985) 1639–1648).

While these publications do indicate that certain different tissues can be targeted in the construction of a transgenic animal, there is no suggestion of the desirability of any particular tissue for commercial production of polypeptide-containing substances. Neither do they suggest any particular gene which is expressed in a given tissue and which would serve to target the expression of the inserted DNA.

A number of factors must be taken into consideration with regard to the substance comprising the peptide and the tissue to which its expression is to be directed. Many proteins require extensive post-translational modification in order to exhibit full biological activity. For example, factor IX requires gamma-carboxylation of a specific subset of glutamic acid residues for biological activity (De Scipio and Davie, *Biochemistry* 18 899–904 (1979)). Liver, which is the site of natural synthesis of factor IX, is proficient in performing this modification. Fibroblasts are capable of carrying out gamma carboxylation of factor IX, although less efficiently: de la Salle et al *Nature* 316 268–270 (1985). However, certain proteins may be correctly modified only if synthesised in a specific tissue and, in some cases, it may be necessary to tailor the site of expression to the requirements of the proteins produced. It is believed that the use of the mammary gland as a tissue for expression overcomes, either wholly or to a satisfactory degree, this potential source of difficulty.

Harvesting from body fluids as opposed to solid tissue is desirable, because such routes are by and large renewable, and most proteins of biomedical importance are themselves-secreted into body fluids. Secretion into the bloodstream is a possible route, either from liver or B lymphocytes, but the coagulant properties of blood and the presence of biologically active peptides and antigenic molecules may prove a hindrance to subsequent downstream processing.

The above difficulties may be overcome in accordance with the present invention by the use of the mammary gland as a tissue of expression. Milk is readily collected, available in large quantities and well characterized biochemically. Further, the major milk proteins are present in milk at high concentrations (from about 1 to 15 g/l).

There are four species of common farm animal in many countries of the world: pigs, goats, sheep and cattle, that is to say members of the family Suidae, the genus Capra, the genus Ovis and the genus Bos. Domesticated cattle are generally of the species Taurus.

While the present invention is not in its broadest aspect restricted to any particular species, genus or family of mammals, pigs, goats, sheep and cattle are preferred. Each has advantages and disadvantages in the context of the present invention. Some of these considerations stem from the fact that, according to a preferred aspect of the present invention, the DNA sequence coding for the polypeptide is incorporated in vitro into a whey protein gene which is expressible in the mammary gland of an adult female mammal to form a fusion gene and the fusion gene is injected into a fertilized egg of the mammal, whereafter the injected fertilized egg is allowed to develop into an adult female mammal.

Although the high milk yield obtained from cattle is a factor tending to suggest that the use of cattle would be preferred, the technical difficulties in manipulating the bovine embryo are greater than in the case of sheep, for example. Furthermore, the sheer cost of experiments involving cattle mean that the other three preferred species of domestic farm animals are the ones of choice.

Table 1 below shows how pigs, sheep and cattle compare with each other for the purposes of use in the present invention.

TABLE 1

Comparison of Different Livestock for Embryo Manipulation and Milk Production.

|  | PIG | SHEEP | CATTLE |
| --- | --- | --- | --- |
| Possibility of controlling time of follicile maturation | Yes | (Yes) | (No) |
| No. of oocytes per animal; no superovulation | 10 | 1 to 3 | 1 |
| No. of oocytes per animal; superovulated | 15 to 20 | 4 to 10 | possibly 6 |
| Visualisation of pronuclei | (Yes) | (Yes) | (No) |
| Seasonal breeding | No | Yes | No |
| Relative cost per embryo transfer, including nominal cost of animals, per embryo | 1.0 | 1.8 | 110 |
| Milk yield, litres/day at peak production | n.a. | 1 to 3* | 5 to 30* |

*Depending on breed.
n.a. = data not available

The significance of the visualisability of the pronuclei is that it is a preferred feature of the present invention to inject the fusion gene containing the DNA sequence coding for the peptide into the pronucleus of the fertilised egg.

Milk yield data for pigs are not readily available, but in sheep, the rate of milk production falls within the range of from 1 to 3 liters per day, depending on the breed. It is of note that specialized equipment for harvesting milk from sheep is available from commercial suppliers, as of course it is for cattle. Sheep are therefore the animals of choice, in particular dairy sheep such as East Frieslands. A strain obtained by crossing a suitable high milk producing line within Blackface sheep is seen as a viable alternative.

The lactating mammary gland is a highly specialized organ comprising an extensive system of ducts that drain complex lobules of secretory cells. Mammary cells are adapted in many ways to high rates of secretion. For example, they have specialized transport mechanisms that ensure the efficient uptake of precursors from the blood, and an extensive system of intracellular membranes (rough endoplasmic reticulum, Golgi apparatus etc.) that enable high rates of protein synthesis, post-translational modification and export from the cell.

The mammary gland is dependent on hormones for all aspects of its growth and function. Review articles on the mammary gland include those by Topper and Freeman, *Physiol Rev* 60 1049–1106 (1980) and Forsyth in "The Biochemistry of Lactation", Mepham (Ed), Elsevier (1982) 309–349. The hormones affecting the mammary gland mediate the striking changes that occur in the gland during pregnancy and lactation. In the ewe, for example, this leads to a near-doubling in total cell number as well as to changes in the proportions of the various cell types and to the terminal differentiation of the secretory cells.

The mammary gland secretes a number of different proteins into the milk. There are qualitative and quantitative differences in the composition of milk from different species, although a general distinction can be made between the caseins and the soluble (whey) proteins (see Jenness in "Developments in Dairy Chemistry, I", Fox (Ed) Elsevier (1982) 87–109). The major ruminant whey proteins that are synthesised in the mammary gland are alpha-lactalbumin and beta-lactoglobulin.

There are three major types of casein. These are alpha-casein, beta-casein and kappa-casein and appear in most of the species characterized. In milk, they serve to sequester calcium with which they are aggregated in the form of micelies. The function of beta-lactoglobulin, the major whey protein in ruminants, is unknown, although it appears to interact with kappa-casein (Brunner, *J. Dairy Sci.* 64 1038–1054 (1981)). Alpha-lactalbumin is an essential cofactor in the conversion of glucose and galactose to lactose (Brew, *Nature* 223 671–672 (1969)). Table 2 shows the protein composition of various milks.

TABLE 2

Protein composition of Various Milks

| g/litre | Bovine | Ovine | Murine | Human |
|---|---|---|---|---|
| CASEINS | | | 7 | |
| Alpha S1 | 10 | 12 | | |
| Alpha S2 | 3.4 | 3.8 | | 0.4 |
| Beta | 10 | 16 | | 3 |
| Kappa | 3.9 | 4.6 | | 1 |
| MAJOR WHEY PROTEINS | | | | |
| Alpha lactalbumin | 1 | 0.8 | trace | 1.6 |
| Beta lactoglubulin | 3 | 2.8 | no | no |
| Whey acidic protein | no | no | 2 | no |
| OTHER WHEY PROTEINS | | | | |
| Serum albumin | 0.4 | . | . | 0.4 |
| Lysozyme | trace | . | . | 0.4 |
| Lactoferrin | 0.1 | . | . | 1.4 |
| Immunoglobulins | 0.7 | . | . | 1.4 |

For the most part it is believed that the different milk proteins are encoded by single copy genes (Mercier and Gaye in "The Biochemistry of Lactation", Mepham (Ed) Elsevier (1983) 177–225 ). The casein genes appear to be linked both in the mouse (Rosen et al *Biochem Soc Trans,* 9 112 (1982)) and in the cow (Grossclaude *Proc. 16th Intl. Conf. Animal Blood Groups Biochem. Polymorphy.* 1 54–59 (1979)). Because the casein genes appear to be expressed at a far higher level than the whey protein genes, it would naturally be thought that the casein genes would be the genes of choice in which to incorporate the foreign DNA for expression. However, contrary to the general expectation, the present invention provides that the DNA sequence coding for the peptide of interest be incorporated into a gene coding for a whey protein.

The gene for rat alpha-lactalbumin comprises four exons and encompasses 2.5 kb of chromosomal DNA ( Qasba and Safaya *Nature* 311 377–380 (1984)). The gene for bovine alpha-lactalbumin appears to be similarly organised. It has now been discovered that ovine beta-lactoglobulin is most probably a single copy gene and comprises seven exons within a 4.9 kb transcription unit: this gene is the gene of preference for use in the present invention.

Changes in the levels of milk protein mRNAs during mammary development in the rat (Nakhasi and Qasba, *J. Biol. Chem* 254 6016–6025 (1979)), rabbit (Shuster et al *Eur. J. Biochem.* 71 193–199 (1976)) and mouse (Pauley et al *Nature* 275 455–457 (1978)) have been assessed using both in vitro translation and cDNA hybridisation. The mammary gland accumulates some 80,000 to 100,000 molecules of milk protein-specific mRNAs resulting from a coordinated mechanism comprising both a high rate of milk protein mRNA synthesis and an efficient stabilisation of these molecules (Mercier and Gaye, op. Cit. and Guyette et al *Cell* 17 1013–1073 (1979)). There are, however, exceptions. In the ewe beta-casein makes up 45% of the total milk protein, yet only 17% of cDNA clones isolated from a cDNA library corresponded to this gene (Mercier et al *Biochimie* 67 959–971 (1985)). In the rabbit, the amount of alpha-lactalbumin sequestered into microsomal vesicles was much lower than that expected from the rate of protein synthesis in the absence of microsomal vesicles, possibly suggesting that the signal peptide does not have an optimal configuration (Gaye et al *Biochimie* 64 173–184 (1982)). The primary translation products of many of the milk protein genes are extensively modified. For example, alpha-lactalbumin is N-glycosylated, kappa-casein is O-glycosylated and alpha- and beta-casein are O-phosphorylated. In addition to its role in post-translational modification, the Golgi complex is also involved in condensing and packaging caseins into micelies. It is a possibility that the caseins and the whey proteins are exported from the cell by different routes. In this regard it is of interest to note that, in both inter- and intra-specific comparisons, the casein signal peptide (in comparison to a large proportion of the rest of the molecules) is highly conserved, suggesting that it may play a role in targeting the nascent peptide into the correct secretory pathway (Mepham et al op cit). As described above, milk protein genes are abundantly expressed in the lactating mammary gland. In the ewe, for example, alpha$_{S1}$-casein mRNA accounts for about 30%, and beta-lactoglobulin accounts for about 5%, of polyA+RNA (Mercier et al (1985) op cit). Given that these transcripts originate from single copy genes, then these levels indicate high rates of transcription and efficient mRNA stabilisation (Teyssot and Houdebine, *Eur. J. Biochem.* 110 263–272 (1980)). Specific mRNA stabilisation may be mediated by sequences present in the mature mRNA. In preferred embodiments of the present invention, similar levels of expression of the DNA sequence that is inserted into the ovine germ line may be achievable. This is accomplished by linking it to the DNA sequences associated with a milk whey protein gene that mediate the high levels of tissue-specific expression and mRNA stabilisation: beta-lactoglobulin is the gene of preference.

Transferring new genes into mice is now a routine procedure. In transgenic mice that exhibit high levels of tissue specific expression of a foreign gene, the exogenous DNA comprises not only the structural gene but also the 5' and 3' flanking sequences. Although there is an abundance of evidence suggesting that many important regulatory elements are located 5' to the mRNA cap site (see for example McKnight and Kingsbury, *Science* 217 316–324 (1982); Payvar et al *Cell* 35 381– 392 (1983); Renkawitz et al *Cell* 37 503–510 (1984); Karin et al *Nature* 308 513–518 (1984)) it is also evident that important regulatory sequences, particularly those mediating tissue-specific expression, may reside within the structural gene or even 3' to it (Charnay et al *Cell* 38 251–263 (1984); Gillies et al *Cell* 33 717–728 (1983)). Furthermore exonic sequences (i.e. those present in mature mRNA) may contain sequences that mediate mRNA stability. Table 3 illustrates some details of tissue-specific expression of foreign genes in mice.

TABLE 3

| Authors | Construct | No. egg re-implanted | DNA copies injected | Transgenic Progeny | Germline Transmission | Expression | Site of Expression |
|---|---|---|---|---|---|---|---|
| Gordon et al PNAS 77 7380–7384 (1980) | PR-SV40 + havTK Cir, Vec | 'sev 100s' | 50–12,000 | 2/173 | nd | nd | |
| E. Wagner et al PNAS 78 5016–5020 (1981) | hBG, hav TK | ns | 2,500 | 5/33 | nd | + | |
| Brinster et al Cell 27 233–231 (1981) | PR-mYT + havTK Cir, Vec, U1700 | 240 | 200 | 7/41 | nd | 4/7 | liver, kidney |
| T. Wagner et al PNAS 78 6376–6380 (1981) | raBG 1. Cir, Vec 2. Lin, Nov | 211 | 20,000 | 7/46 | + | + | |
| Costantini & Lacy Nature 294 92–94 (1981) | raBG Lin, Vec, U14000+ | ns | 100–1000 | 9/24 | 4/4 | nd | |
| Gordon & Ruddle Science 214 1244–1246 (1981) | hIFN (alpha) (cDNA) Cir, Vec | ns | 10,000 | 1/10 | + | nd | |
| Palmiter et al Cell 29 701-71- (1982) | PR-mMT + hsvTK Cir/Lin, Vec/Nov (U1700) | ns | 200–600 | 10/69 | + | 7/10 | primarily liver |
| Palmiter et al Nature 300 611–615 (1982) | PR-mMT + rGH | 170 | 600 | 7/21 | nd | + | primarily liver, express hypervariable |
| McKnight et al Cell 34 335–341 (1983) | cTransferrin 1. Cir, Vec 2. Lin, Vec U2000 | ns | 1. 500 2. 140 | 3/19 | + | 6/7 | liver, kidney (tail, testes weak expression) |
| Lacy et al Cell 34 343–356 (1983) | raBG Lin, Vec, U14000+ | ns | 100–1,000 | 9/24 | 8/9 | 2/9 | muscle or testis |
| Palmiter et al Science 222 809–814 (1983) | PR-MT + hGH Lin (Vec) U230 | 1000 | 1,000 | 33/101 | nd | + | primarily liver |
| Brinster eta al Nature 306 332–336 (1983), Storb et al Nature 311 65–67 (1984) | mIgK (lit) or hGH Lin, Nov U185 | 192 | 400 600 | 6/11 7/41 | 4/4 | + | spleen/B-lymphocytes (1 × kidney) |
| Brinster et al Cell 37 367–379 (1984) | PR-SV40 + svT Lin, Vec | 925 | 240–830 | 25/95 | — | + | brain tumours |
| Swift et al Cell 38 639–646 (1984) | rElastase type I Lin, (Vec) | 320 | 200 | 7/37 | 7/7 | 5/5 | exclusively pancreas |
| Grosschedl et al Cell 38 647–658 (1984) | mIgM hev (functionally re-arranged) Lin, Vec, U2000 | 284 | 50 | 5/13–23 | 3/4 | 4/5 | primarily (exclusively) B and T lymphoc |
| Stewart et al Cell 38 627–637 (1984) | PR-mMTV + mMYC Lin, Vec, U2000 | ns | 500 | 13 | nd | 11/12 | primarily salivary gland (mammory tumour) |
| Ornitz et al Nature 313 600–602 (1985) | PR-rElastase type I + hGH Lin, Vec, U200 | ns | nd | 22/131 | nd | 13/18 | exclusively pancreas |
| Shani Nature 314 283–286 (1985) | rHyosin lit-2; Lin, Vec, U1200 | ns | 500 | 4/26 | 3/4 (1 mosaic) | 2/4 | exclusively skeletal mu |
| Rusconi & Kohler Nature 314 330–334 (1985) | rIgM hev & lit (K) (finctionally rearranged) Cir, Vec, U3000–U5000 | ns | 20–100 | 5/13 | 4/5 (1 mosaic) | 5/5 | B lymphocytes |
| Chada et al Nature 314 377–380 (1985) | PR-mBG + hBG Cir, Vec or Lin, Nov U1200 | ns | 400–800 | 10 | nd | 4/10 | primarily erythroid cells low expression |
| Hanahan Nature 315 115–121 (1985) | PR-rInsulin II +svT Lin, Vec, (Lin, Nov) | ns | 20–150 | 5 | 5/5 | + | exclusively pancreas (B cell tumours) |

Cir = injected with circular DNA;
Lin = DNA linearised before transfer;
Nov = vector removed before transfer;

TABLE 3-continued

| Authors | Construct | No. egg re-implanted | DNA copies injected | Transgenic Progeny | Germline Transmission | Expression | Site of Expression |
| --- | --- | --- | --- | --- | --- | --- | --- |

Vec = Vector present during transfer;
U = upstream sequences;
U1000 = 1000 bp of U sequences
c = chicken;
h = human;
hsv = herpes siplex virus;
m = mouse;
r = rat;
ra = rabbit;
sv = simian virus 40
BG = bea globin;
GH = gorwth hormone;
IFN = interferon;
Ig = immunoglobin;
PR = promoter;
T = T antigen;
TK = thymidine kinase;
hev = heavy chain;
lit = light chain;
nd = not determined;
us = not specified.

It is for the above reason that the above preferred fusion genes that will be used to direct the expression of the DNA sequence coding for the peptide of interest will comprise one or more of: a promoter; a start site for transcription; one or more (presumed) distal 5' regulatory sequences of a milk protein gene; structural milk protein gene sequences; 3' sequences flanking a milk protein gene. The most preferred fusion genes comprise sequences of all these types.

A fusion gene of choice will consist of a cDNA sequence coding for the peptide of interest inserted into the first exon of a whey protein gene. It is preferred that several kb of the 5' flanking sequences of the milk protein gene will be included in such a fusion gene. In these constructs, secretion of the peptide of interest will preferably be mediated by its own signal peptide; it is therefore preferred that the fusion gene contain a signal peptide for the peptide of interest. However, a tissue-specific signal peptide may be important for targeting the nascent peptide into the correct secretory pathway (as discussed above). Therefore, it is particularly preferred that DNA sequences encoding the signal peptide of the whey protein gene will be precisely fused to the DNA sequences of the insert that encode the N-terminal amino acid of the mature protein. The 3' end of the insert will preferably terminate after its stop codon, but before its own message cleavance and polyadenylation site. Downstream of the site of insertion, the rest of the structural gene will generally be retained, as well as some 3' flanking sequences.

In a transgenic animal, such a construct should maximise the chances of obtaining high levels of mammary gland-specific expression. The primary transcript should be correctly polyadenylated and spliced at the sites retained in the whey protein gene. The mature message should contain sequences for efficient stabilisation of mRNA. In constructs employing the milk gene signal peptide, the mature mRNA should be translated to yield a fusion pre-peptide in which the signal peptide derived from the milk protein gene efficiently directs the secretion of the mature peptide encoded by the cDNA insert.

Ovine beta-lactoglobulin is, as discussed above the whey protein gene of choice with which to "entrain" cDNA coding for the peptide of interest. In sheep, beta-lactoglobulin is the most abundantly expressed whey protein in the mammary gland and its mRNA comprises about 8% of the total polyA+ RNA. The gene has been well characterized and used to elaborate fusion contructs with cDNA sequences encoding human factor IX and human alpha1 antitrypsin.

According to a second aspect of the present invention, there is provided a genetic construct comprising a DNA sequence encoding a peptide incorporated into a gene of a mammal coding for a milk whey protein in such a way that the DNA sequence is expressible in the mammary gland of the adult female mammal.

According to a third aspect of the present invention, there is provided an animal cell including a genetic construct as described above. The animal cell may be an embryo cell.

According to a fourth aspect of the present invention, there is provided a plasmid comprising a genetic construct as described above.

Preferred features of the second, third and fourth aspects are as described above for the first aspect, *mutatis mutandis*.

For the better understanding of the present invention, a number of examples will now be given. In the examples, reference will be made to the drawings in which.

EXAMPLE 1

A. RECOMBINANT DNA PROCEDURES

Figure 1:
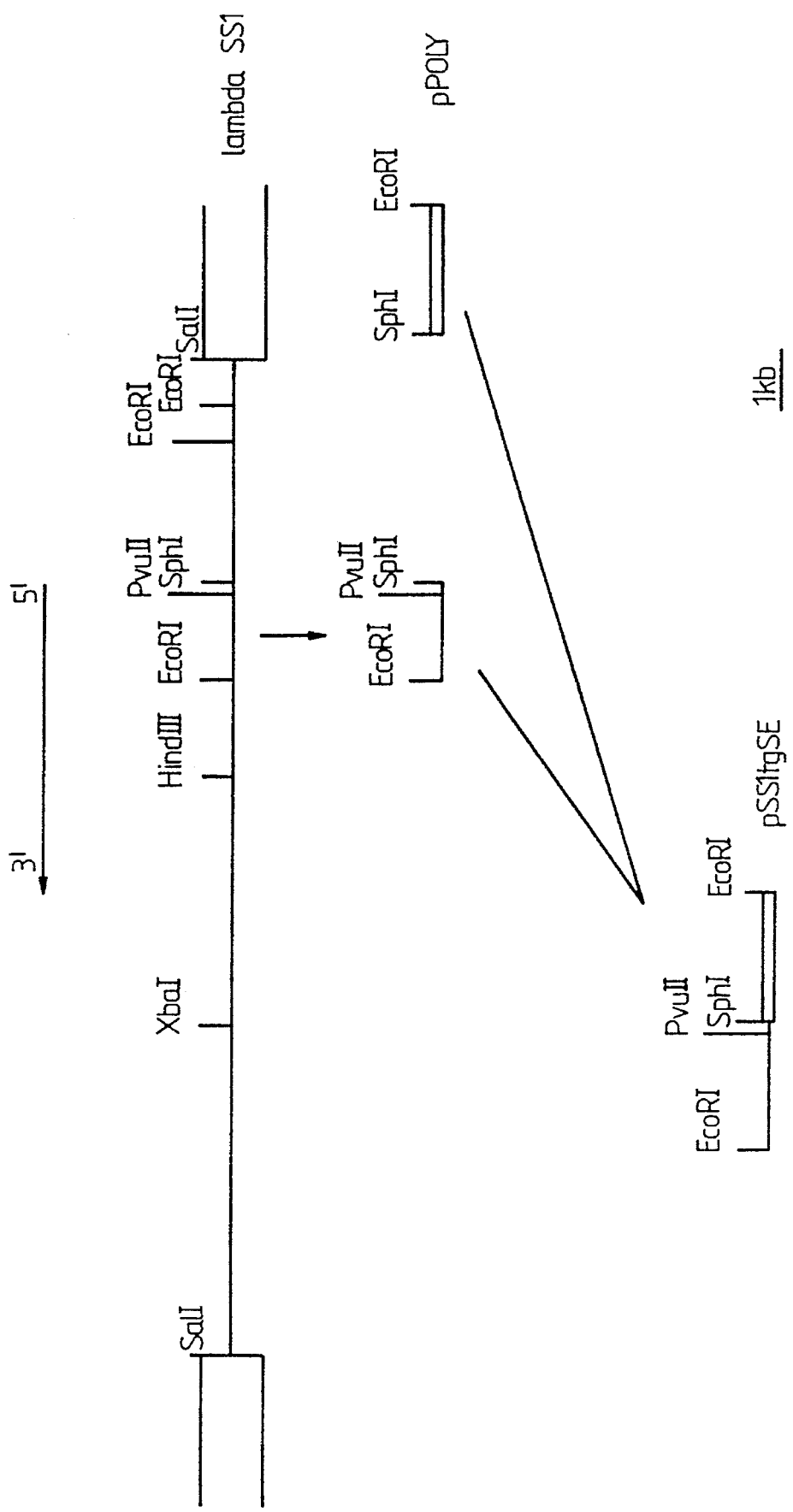
FIGS. 1 to 4 show schematically the basic steps in the elaboration of a beta-lactoglobulin fusion gene in a method in accordance with the present invention.

Where not specifically detailed, recombinant DNA procedures were after Maniatis et al ("Molecular Cloning" Cold Spring Harbor (1982)) and "Methods in Enzymology" Vols 68, 100 and 101 (Wr, Grossman and Moldave, Eds. ), Academic Press; and, unless specifically stated, all chemicals were purchased from BDH Chemicals Ltd, Poole, Dorset, England or the Sigma Chemical Company, Poole, Dorset, England.

CONSTRUCTION OF OVINE BETA-LACTOGLOBULIN FUSION GENES

Preparation of Sheep Spleen DNA

Spleen tissue was procured from a freshly slaughtered Blackface/Suffolk lamb and nuclei were isolated essentially as described by Burch and Weintraub Cell 33 65 (1983). Nuclear pellets were lysed in 0.3M NaCl, 10 mM Tris.HCl, 10 mM EDTA, 1% SDS pH 7.4 and 400 mcg/ml Proteinase K (Sigma Co, Fancy Road, Poole, Dorset BH17 7NH) and incubated for two hours at 37° C. Repeated phenol/chloroform extractions were performed until the preparation was completely deproteinised. The DNA was ethanol precipitated and spooled out using a glass rod, washed with 70% EtOH/30% TE (TE=10 mM Tris.HCl, 1 mM EDTA pH 8.0), dried in air and resuspended in TE to a concentration of 1 mg/ml.

Construction of Sheep Spleen DNA Lambda Fusion Genes

The lambda phage EMBL3 (Frischauf et al J. Mol. Biol. 170 827 (1983)) was employed to construct the genomic library. 30 mcg of bacteriophage DNA were digested with 5-fold excesses of the restriction enzymes EcoRI and BamHI (supplied by Amersham Intgernational plc, Lincoln Place, Green End, Aylesbury, Buckinghamshire, England) using the conditions recommended by the manufacturer. After digestion, spermine hydrochloride was added to a concentration of 5 mM to precipitate the lambda DNA. After incubation for one hour on ice the DNA was pelleted at 10,000 g for 15 minutes in a bench microfuge, washed in 70% EtOH, 300 mM NaAc, 100 mM $MgCl_2$, repelleted and finally resuspended in TE at a concentration of 1 mg/ml.

Sheep DNA was partially digested with the restriction enzyme Sau3A (Amersham). 100 mcg aliquots of the sheep DNA were digested with varying amounts of Sau3A [from 5–40 units] for 20 minutes at 37° C. The reactions were stopped by the addition of EDTA to 15 mM. The degree of digestion was assessed by electrophoresis on 0.6% agarose gels. Suitably digested samples were pooled and loaded onto 38.0 ml 10–40% sucrose gradients made up in 1M NaCl, 20 mM Tris.HCl, 5 mM EDTA at pH 8.0. These gradients were centrifuged in a Beckmann SW 28 rotor at 26,000 rpm for 24 hours. The sucrose gradients were fractionated from the top and 1 ml fractions collected. The size distribution of DNA molecules in each fraction was assessed by agarose gel electrophoresis, and fractions containing DNA molecules from 14–21 kb in size pooled. After a two-fold dilution in TE 2 volumes of EtOH were added and the DNA precipitated overnight at −20° C. The DNA was subsequently resuspended in TE to a concentration of 300 mcg/ml.

7.5 mcg of BamHI/EcoRI cut EMBL3 and 2.5 mcg of sheep spleen DNA which had been partially digested with Sau3A were mixed together in 50 mcl of a solution containing 60 mM Tris.HCl, 6 mM $MgCl_2$, 10 mM DTT, 0.01% gelatin, 0.25 mM rATP and 25 units of $T_4$ DNA ligase (Boehringer Company, Boehringer Mannhelm House, Bell Lane, Lewes, East Sussex) and incubated overnight at 14° C.

After ligation 1 mcg aliquots of the DNA were packaged in vitro using a kit purchased from Amersham following the recommended procedure of the manufacturer. The packaged library was titred on E. coli strain ED 8654. The estimated size of the library was $5.7 \times 10^6$ plaque forming units (pfu's). Immediately after titration, aliquots of the unamplified library were plated onto $10 \times 22$ cm$^2$ petri dishes (megaplates) using E. coli strain ED 8654 at a density of approximately 50,000 pfu's/plate.

Screening the Lambda Genomic Library

Plaque-lifts from the mega-plates were performed according to the method of Benton and Davis (Science 196 180 (1977)) onto 20 cm$^2$ nitrocellulose membranes (Schleicher and Schull, Postfach 4, D-3354, West Germany). A beta-lactoglobulin cDNA clone (p931—gift of J. C. Mercier, INRA, Jouey-en-Josas, Paris) was nick translated with $^{32}P$ dCTP to a specific activity $>10^8$ dpm/mcg, by the method described by Rigby et al (J. Mol. Biol. 113 237 (1977)). Beta-lactoglobulin cDNA may be cloned as described by Mercier et al in Biochimie 67 959–971 (1985). The sequence of the p931 clone is given by Gaye et al in Biochimie 68, 1097–1107 (1986).

Filters were prehybridised, hybridised and washed according to the method of Maniatis et al in Cell 15 687 (1978). The final wash was in 1×SET at 68° C. (SET is 0.15M NaCl, 2 mM EDTA, 0.03 m Tris.HCl pH 8.0). Filters were blotted dry and spotted with $^{32}P$ to orientate them before exposure to X-ray film. Regions containing positively hybridising plaques were positioned on the megaplates by reference to the $^{32}P$ spots picked using the sterile blunt end of a Pasteur pipette. The initial plaque lifts were titred on E. coli ED 8654 and plated onto 15 cm diameter Petri dishes at a plaque density of approximately 500/plate. These plates were rescreened by the procedures described above and individual positively hybridising plaques were picked using a toothpick into 1.0 ml of phage-buffer (phage buffer is 10 mM Tris.HCl, 10 mM $MgCl_2$, 0.01% gelatin, pH 7.4).

Preparation of Cloned Beta-Lactoglobulin DNA 0.4 ml of the resuspended phage solution was added to E. coli ED 8654 (Borg et al Mol. Gen. Genetics 146 199–207 (1976)) and plated out on 9 cm diameter Petri dishes to obtain confluent -ysis of the bacterial lawn. Confluent plates were obtained from which the top plating agar was scraped off into 10 ml of phage buffer and incubated overnight with a few drops of chloroform. The bacterial debris was pelleted by centrifugation at 5000 rpm for five minutes and the phage stocks stored at 4° C. The stocks were titrated on E. coli ED 8654 to determine the pfu/ml.

$8 \times 10^7$ pfu's were absorbed onto $7 \times 10^9$ E. coli cells in 10 ml of 10 mM $MgSO_4$ at 37° C. After 15 minutes, 2.5 ml aliquots were added to 100 ml L Broth/10 mM $MgSO_4$ in a one liter flask. The bacterial suspension was shaken vigorously for several hours and the $OD_{540}$ was monitored every hour. Lysis, as determined by a fall in the $OD_{540}$, occurred after several hours. When complete, 0.2 ml chloroform was added to each 100 ml culture and the culture left at 4° C. overnight.

The bacterial debris was removed by centrifugation at 10,000 rpm for 15 minutes. 10 mcg/ml RNAase A and 10 mcg/ml DNAase I were added to the supernatant which was then incubated at 37° C. for one hour. After this incubation NaCl was added to 40 g/liter and polyethylene glycol (PEG) to 10%. The preparation was cooled to 4° C. and left for at least two hours to precipitate the phage. The phage pellet was pelleted at 10,000 rpm for 15 minutes and resuspended in 16.0 ml of phage buffer. 8.0 ml of this suspension was layered upon a step gradient comprising 1.5 ml 56% CsCl, 1.5 ml 45% CsCl and 2.5 ml 31% CsCl (dissolved in phage buffer) in a 14.0 ml ultracentrifuge tube. The step gradients were centrifuged at 35,000 rpm for 1.5 hours in a swing-out rotor at 20° C. The phage band was removed with a needle and syringe and, to complete the purification of the phage particles, a second step gradient centrifugation was performed.

The purified phage particles were dialysed into 0.1M NaCl, 10 mM Tris.HCl, 1 mM EDTA pH 8.0 and then deproteinised by successive extractions with phenol and chloroform. NaCl was added to a final concentration of 0.3M and then the phage DNA precipitated by the addition of 2 volumes of EtOH. The DNA was pelleted by centrifugation at 10,000 rpm for 20 minutes, washed with 70% EtOH, 30% TE, dried and then resuspended in TE to a final concentration of 200–400 mcg/ml.

Characterisation of Recombinant
Beta-Lactoglobulin Clones 0.5 mcg aliquots of the DNA preparations described above were restricted with a variety of restriction enzymes and the products of the single and double digests analysed by electrophoresis on 0.6% and 1% agarose gels. DNA on these gels was transferred to nitrocellulose filters on to Hybond membranes (Amersham International, Little Chalfont, Bucks) by the method of Southern (*J. Mol. Biol.* 98 503 (1975)) and hybridised to $^{32}$P labelled p931. The procedure used was essentially as described above and the hybridised filters were analysed by autoradiography. Using a variety of restriction enzymes and specific probes from the 5' and 3' ends of p931 a restriction map was constructed in which the size and orientation of the beta-lactoglobulin gene(s) was determined, (see FIG. 1).

The identity of the beta-lactoglobulin clones and the precise position of the 5' and 3' ends of the gene were directly confirmed by DNA sequencing. Using suitable restriction sites, fragments were subcloned into plasmid vectors and into M13 vectors. Sequencing was carried out using the dideoxy method of Sanger et al. (PNAS 74 5463 (1977)).

Elaboration of Beta-Lactoglobulin Fusion Genes

The strategy used for elaborating fusion genes comprising beta-lactoglobulin and genes of interest to be expressed in the mammary gland is outlined in FIGS. 1 to 4. The approach utilises sequences derived from a lambda clone, whose isolation and characterisation is described above. The strategy involves insertion of the DNA sequence of interest into the region of DNA corresponding to the 5' untranslated region of beta-lactoglobulin mRNA. Proteins translated from mRNA transcripts of this gene will contain the secretory peptide of the target protein.

The subclone pSS-1tg SE was constructed as shown in FIG. 1 by ligating the 1.4 kb SphI-EcoRI fragment of lambda phage SS-1 into the vector plasmid pPoly which had also been cut with SphI+EcoRI and *E. coli* strain DH1 transformed having been made competent by the procedure of Hanahan and Meselson (*Gene* 10 63 (1980)). Ampicillin resistant clones were isolated and DNA prepared from them by the method of Birnboim and Doty (*Nuc. Acid Res.* 7 1513 (1979)).

In FIG. 1, the top arrow defines the orientation and extent (approximately 4.9 kb) of the beta-lactoglobulin transcription unit present within lambda SS1; the scale is the same throughout. More generally, in FIGS. 1 to 4, it should be noted that only relevant restriction sites are shown. Large open boxes represent lambda EMBL3 arms; narrow open boxes represent pPoly; the narrow shaded box represents the target sequence to be expressed; lines represent cloned sheep sequences corresponding to the beta-lactoglobulin gene and its flanking sequences.

pSS-1tgSE was linearised by digestion with the restriction endonuclease PvuII (FIG. 2) which cuts at a unique site in the plasmid in a region of DNA corresponding to the 5' untranslated mRNA sequences of beta-lactoglobulin. 5 mcg of completely digested plasmid was dissolved in 0.5M Tris.HCl, 10 mM MgCl$_2$, 1 mM MnCl$_2$, 10 mM spermidine, pH 9.0, and treated with 0.01–0.04 units of calf intestinal phosphatase (Boehringer) for 30 minutes at 56° C. The calf intestinal phosphatase was inactivated in 0.5% SDS and the DNA recovered by phenol/chloroform extractions and EtOH precipitation.

A Factor IX DNA clone p5'G3'CVI was procured from Dr. G. Brownlee, Sir William Dunn School of Pathology, University of Oxford, Oxford. This clone contains a 1579 bp insert in a plasmid derived from pAT153 (Twig et al *Nature* 283, 216–218 (1980)). It runs from the TaqI site at −7 from the presumed mRNA start site to +1572 and contains the entire coding sequence for human Factor IX (Anson et al *Embo J.* 3, 1053–1060 (1984)).

A NheI-HindIII fragment, comprising 1553 bp of Factor IX sequences was excised and purified from the vector sequences by the methods described below. The HindIII and NheI ends of this were blunted using Klenow polymerase by the technique described by Maniatis et al ("Molecular Cloning" Cold Spring Harbor (1982)) and the fragment ligated into PvuII restricted, phosphatased pSS1tgSE (described above) to form pSS1tgSE-Factor IX after transforming *E. coli* DH-1 to ampicillin resistance.

Figure 2:
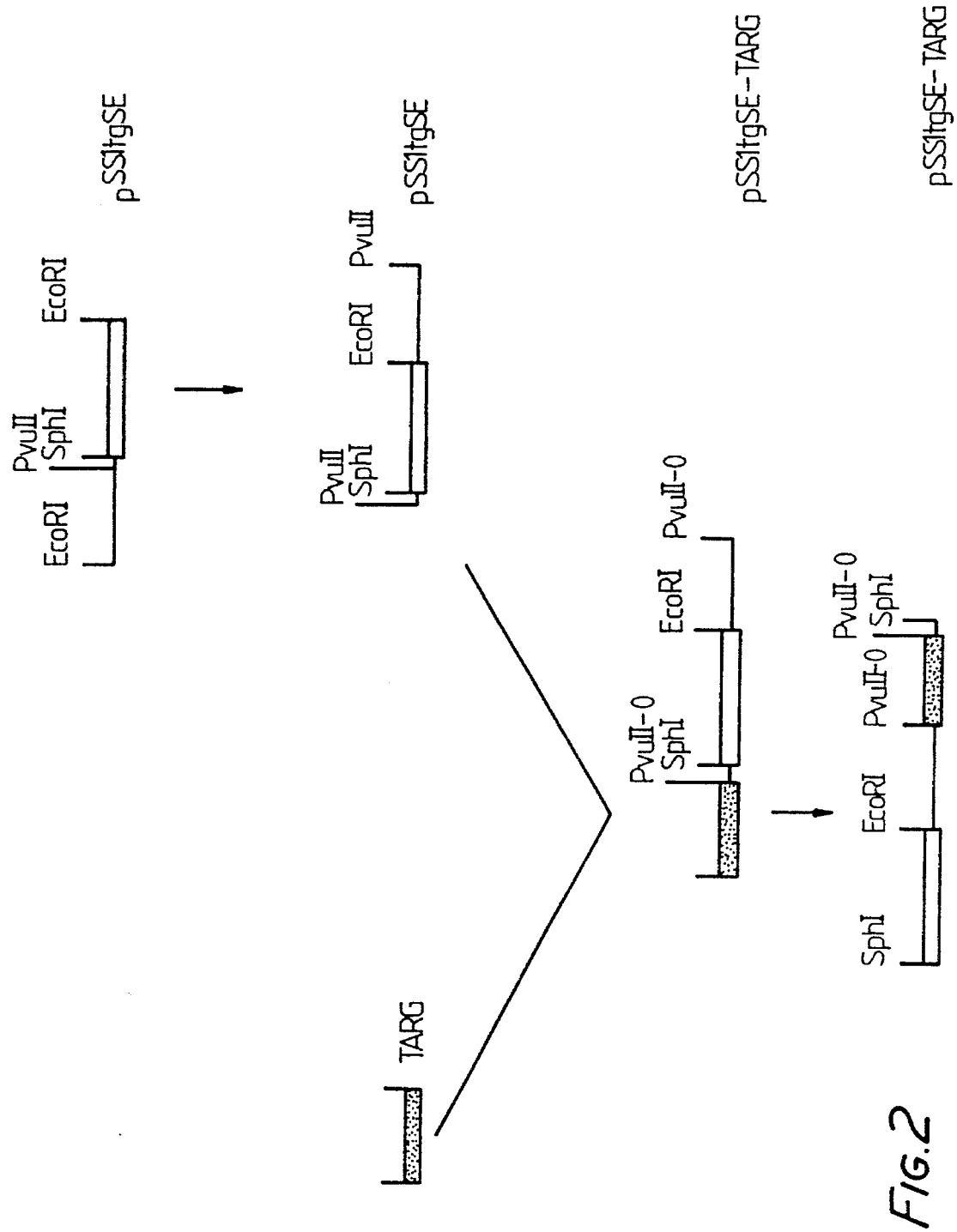
Figure 3:
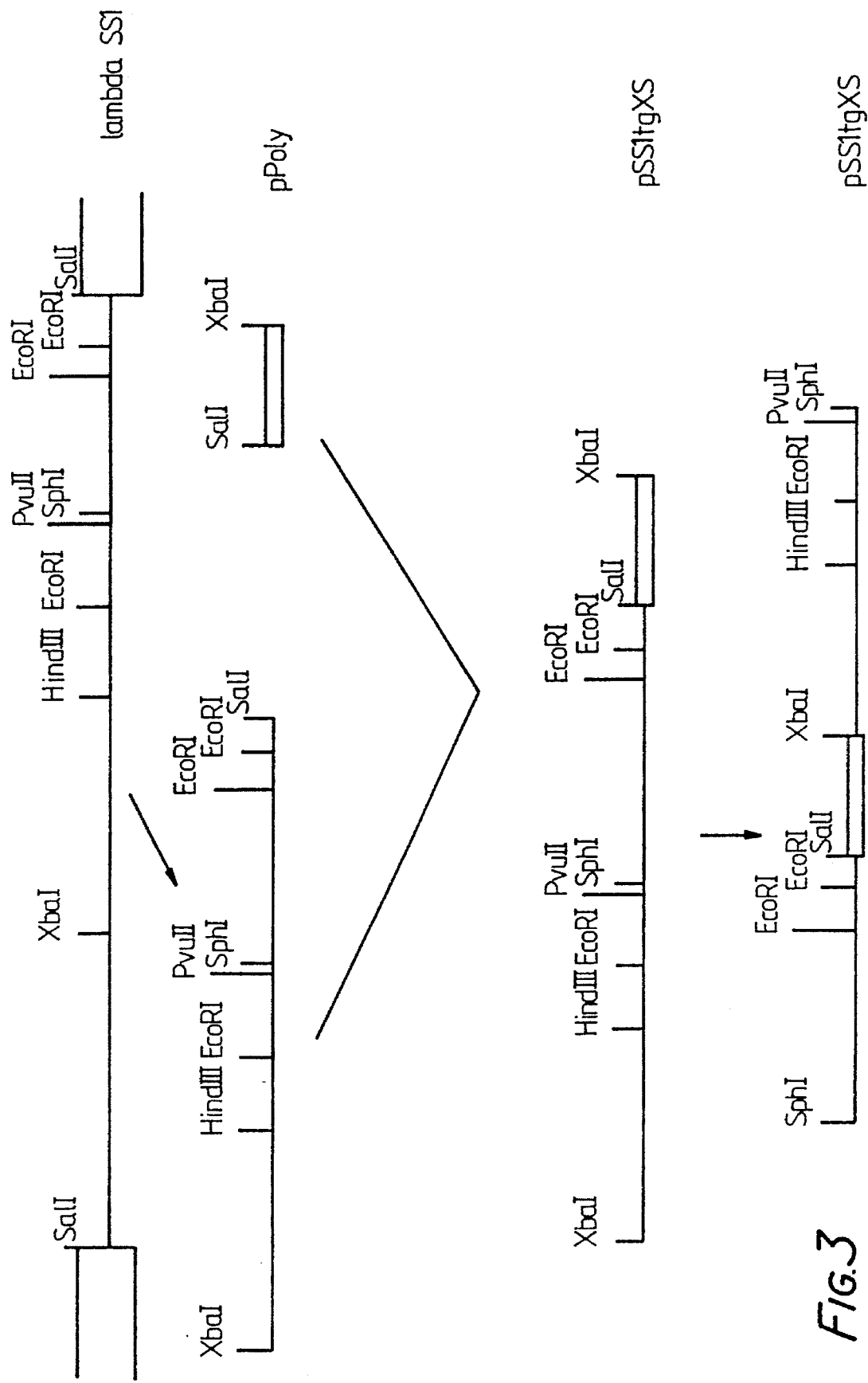

The Factor IX cDNA sequence is hereafter designated TARG, as can be seen in FIG. 2.

Plasmid DNA was prepared as described above and checked by digestion with suitable restriction enzymes. The plasmid DNA was digested with SphI+EcoRI, electrophoresed on a 1% agarose gel containing 0.5 mcg/ml ethidium bromide (Sigma). The relevant SphI-EcoRI fragment was located by illumination with a UV lamp (Ultra-Violet Products, Inc., San Gabriel, Calif., USA). A piece of dialysis membrane was inserted in front of the band and the DNA subsequently electrophoresed onto the membrane. The DNA was eluted from the dialysis membrane and isolated by use of an "Elu-tip" [Schleicher and Schull, Postfach 4, D-3354, Dassel, W. Germany], employing the procedure recommended by the manufacturer.

Figure 4:
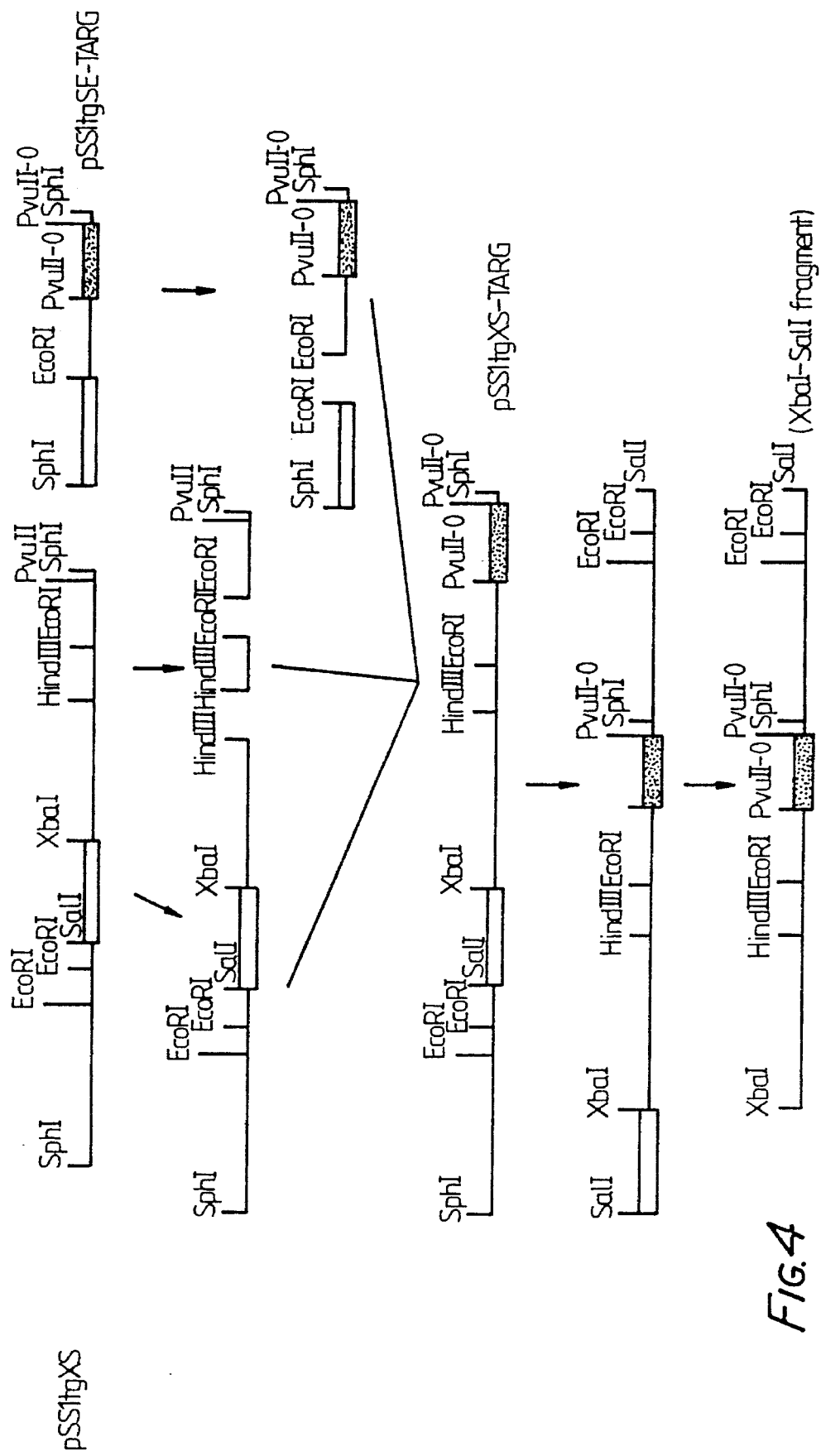

The plasmid pSS1tgXS (FIG. 3) was constructed by ligating the XbaI-SalI fragment of lambda SS-1 into XbaI-SalI digested pPoly. Clones were isolated and plasmid DNA prepared as previously described. Two DNA fragments were independently isolated from this plasmid or smaller subclones derived from it: a 10.5 kb SphI (partial) HindIII fragment and a 1.2 kb EcoRI-HindIII fragment (FIG. 4). These fragments were isolated by gel electrophoresis, as described above.

The SphI-EcoRI, SphI-HindIII, and the EcoRI-HindIII fragments were ligated together in approximately equal ratios and the DNA used to transform DH-1. Plasmid DNA (pSS1tgXS-TARG) was prepared as described above and digested with XbaI and SalI to excise the beta-lactoglobulin fusion gene from the vector. This fragment was purified by gel electrophoresis followed by the use of an "Elu-tip". The ethanol precipitated DNA was pelleted, resuspended in TE and phenol/chloroform extracted and reprecipitated. The DNA was finally resuspended in TE and was employed directly for microinjection.

B. CONSTRUCTION OF TRANSGENIC ANIMALS

Collection of Fertilised Eggs

Procedures were analogous to those described for mice in Gordon and Ruddle in "Methods in Enzymology" (1983) Vol 101 (W, Grossman and Moldave, Eds.) Academic Press pp411 to pp432.

Embryos are recovered from ewes that have been induced to superovulate at an oestrus that is controlled by treatment with progestagen. Mature ewes of proven fertility are treated for 12–16 days with intravaginal sponges that are impregnated with 60 mg medrogproxyesterone acetate (Veromix, Upjohn Ltd. Crawley). Equine follicle stimulating hormone [3.5–4.3 mg in aqueous solution/ewe] is given in 2 equal intramuscular injections 28 hrs before the end of progrestagen treatment and at the time of sponge withdrawal. Ewes are allowed to mate several times at the oestrus that occurs 20–72 hrs after sponge removal. The ewes are observed for the onset of heat at 08.00, 12.00, 16.00 and 20.00 hr daily. Embryos at the 1 to 4 cell stages of development are recovered during surgery 36–72 hrs after the onset of oestrus.

Anaesthesia is induced by intravenous injection of thiopentone sodium [Intraval, May and Baker] and maintained by mixtures of oxygen and nitrous oxide in a semi-closed circuit system. Embryo recovery was carried out by the procedures of Hunter et al (*J. Agric. Sci.* 46 143–149 (1955)). The reproductive tract is exposed through a mid-central incision and a nylon catheter inserted into the oviduct through the fimbria. Medium is introduced into the uterine lumen through a blunted 18-gauge needle and forced through the uterotubal junction and along the oviduct. The embryos are recovered in phosphate-buffered saline containing energy sources and protein [Ovum Culture Medium, Flow Labs, Irvine, Scotland]. During storage and microinjection of eggs this medium is supplemented with 20% foetal calf serum.

Injection of DNA

DNA (1 to 2 mcg/ml) is injected into one pronucleus of single cell eggs or into one or more nuclei of 2 and 4 cell eggs. The eggs are manipulated in a chamber filled with ovum culture medium. The chamber consists of a siliconised microscope slide with glass supports (25 mm×2 mm×3 mm) parallel to the long side of the slide. A coverslip is mounted on top of the supports, the junctions being sealed with silicone grease. The open ends of the chamber are filled with Dow-Corning 200 fluid (50 cs) (BDH Chemicals).

Eggs to be injected are held by suction on a blunt glass pipette. Pronuclei or nuclei are visualised using a Nikon Diaphet inverted microscope (Nikon (UK) Ltd, Haybrooke, Halesfield 9, Telford, Shropshire). DNA is injected into pronuclei or nuclei using a micropipette drawn from capillary tubing (borosilicate glass—1 mm external diameter, thin wall with filament—Clark Electromedical Instruments, PO Box 8, Pangbourne, Reading, RG8 7HU) on a micro-electrode puller (Campden Instruments, 186 Campden Hill Road, London). The positions of the two microinstruments are controlled using micro-manipulators (Leitz Mechanical Micromanipulators, E. Leitz (Instruments) Ltd, 48 Park Street, Luton, England). The micropipette containing the DNA to be injected is connected via air-tight tubing to a 100 ml glass syringe. Injection is performed by application of pressure using the syringe. Successful injection is indicated by visible swelling of the pronuclei or nuclei. The injected eggs are incubated at room temperature for a minimum of 30 minutes to allow visible degeneration of damaged eggs.

Embryos judged to have survived injection are transferred to un-mated recipient ewes whose oestrus cycles are synchronised with those of egg donors by treatment with progestagen [Veromix, Upjohn Ltd]. Embryos are transferred to the oviduct using fine-drawn mouth-pipettes. Up to 4 embryos are transferred to each ewe. The embryos are distributed between the oviducts.

The body-wall of the ewes is closed with soluble filament [Descon, Davis and Greck] and the skin with Michel clips. Each ewe is given antibiotics [Duphapen L.A., Duphar, Amersham] at the time of surgery. The Michel clips are removed 10–20 days after surgery.

Development and Growth

After recovery from anaesthesia the ewes are returned to the paddock where they remain throughout pregnancy. Supplementary hay, turnips and concentrates are provided as required. During the third month of pregnancy the number of fetuses is determined by real ultra-sonic scanning. (White et al *Vet. Rec.* 115, 140–143 (1986)). Management of pregnant ewes is then adjusted to take account of variation in foetal number. As the expected date of parturition approaches the ewes are housed to facilitate supervision and assistance during lambing.

Analysis of Transgenic Lambs

At least 2 weeks after birth 10 ml samples of blood are removed by venous puncture with a hypodermic syringe and collected in a heparinised tube. DNA was prepared from blood samples as follows: 30 ml of lysis solution (155 mM $NH_4Cl$, 10 mM $KHCO_3$, 1 mM EDTA) was added to a 10 ml blood sample and the mixture incubated for 15 minutes on ice. The white blood cells were spun down at 1500 g for 10 minutes at 40° C. resuspended in 10 ml SE (75 mM NaCl, 2 mM EDTA) and then washed once in SE. Proteinase K was added to 100 mcg/ml followed by 1 ml 20% SDS and the preparation incubated for 4 hours. Repeated phenol/chloroform extractions were performed until the preparation was completely deproteinised. 1/30th vol of 0.3M NaAc-1 vol isopropanol were added to the aqueous phase to precipitate the DNA, which was hooked out, rinsed in 70% EtOH and resuspended in TE.

10 mcg aliquots of the DNA preparations were digested with suitable restriction enzymes (eg EcoRI) and electrophoresed on 0.8% gels. These gels were analysed by Southern Blotting and hybridisation was performed essentially as described.

Positively hybridising animals, i.e. those containing the fusion gene (presumed to be integrated at a chromosomal location), are allowed to grow to maturity. Females are mated and, once lactating, their milk analysed for the substance of interest (see Example 7). Positive males are mated and their daughters screened for the exogenous DNA sequences and their milk is subsequently analysed for the substance of interest.

EXAMPLE 2

The procedure of Example 1 is repeated, except that the DNA sequence encoding the polypeptide of interest (the TARG sequence) encodes $alpha_1$-antitrypsin was obtained from R. Cortese, EMBL, Meyerhofstrasse 1, D-6900 Heidelberg, West Germany. A TaqI-BstNI fragment comprising 1294 bp of the insert (see Ciliberto et al *Cell* 41 531–540

(1985)) was excised, purified from this clone and cloned into the PvuII site of pSSItgSE by the methods described in Example 1.

EXAMPLE 3

The procedure of Example 1 is repeated, except that instead of the plasmid pPoly, the plasmid pUC18 (Pharmacia Ltd, Pharmacia House, Midsummer Boulevard, Milton Keynes", England) is used instead.

EXAMPLE 4

The procedure of Example 1 is repeated, except that instead of the plasmid pPoly, the plasmid pUC19 (Pharmacia Ltd, Pharmacia House, Midsummer Boulevard, Milton Keynes", England) is used instead.

EXAMPLE 5

Generation of Transgenic Sheep

The SalI-XbaI fragment, excised from the plasmid pSS1tgXS-FIX (also designated pSS1tgXS-TARG, see Example 1), was injected into sheep eggs. Approximately 200 copies/fertilised egg were injected. From 252 one cell eggs injected and reimplanted into recipient ewes, 52 live lambs were born. Based on the analysis of DNA prepared from blood samples four of these animal were shown to carry the exogenous beta-lactoglobulin-Factor IX sequences (Table 4).

TABLE 4

| Summary of Transgenic Sheep. | | | |
|---|---|---|---|
| LAMB No. | SEX | CONSTRUCT | COPY No. (Approx) |
| 6LL225 | M | BLG-FIX | 40 |
| 6LL231 | F | BLG-FIX | 10 |
| 6LL239 | M | BLG-FIX | 1 |
| 6LL240 | F | BLG-FIX | 10 |

All of the eggs were injected at the pronucleus stage and none were centrifuged.

Copy numbers were determined by quantitative scanning densitometry.

Figure 5:
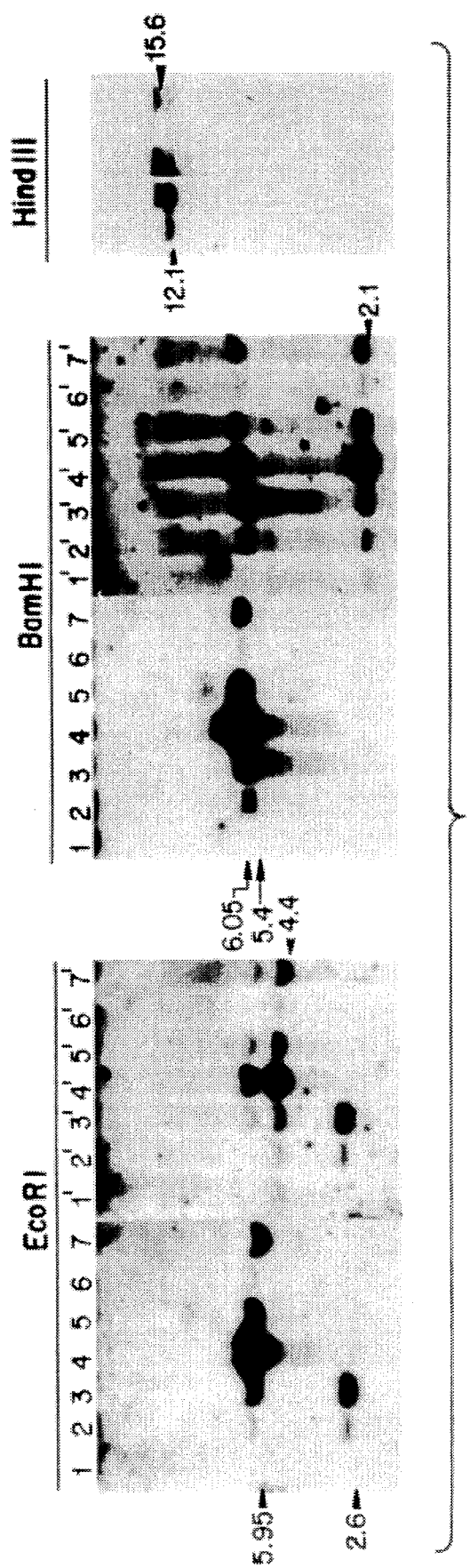
FIG. 5 shows a Southern blot analysis of sheep DNA.

FIG. 5 is a Southern blot analysis of the sheep DNA. Sheep DNA was prepared as described, digested with the restriction enzymes indicated, electrophoresed on a 0.8% agarose gel and transferred to Hybond membrane (Amersham International, Little Chalfont, Bucks, UK). The filter was probed with 32P labelled plasmid pSS1tgXS-FIX (lanes 1–7) and subsequently (after stripping the membranes) with plasmid p931 (lanes 1'–7'). Copy controls of pSS1tgXS-FIX were included on the gel where indicated. Lane 1, control (non-transgenic) sheep DNA; lanes 2 and 3 control DNA plus 1 and 5 copy equivalents of p5'G3'CVI; lanes 4–7, DNA from transgenic sheep 6LL225, 6LL231 , 6LL239 and 6LL240. Each transgenic sheep yields Factor IX hybridising bands of 5.95 kb (EcoRI) and 6.05 kb (BamHI), identical in size to those derived from pSS1tgXS-FIX, showing that the 5' ends of the transgenes are intact. Significant hybridisation with sheep Factor IX was not observed. Hybridisation with p931 revealed the predicted 4.4 kb EcoRI and 2.1 kb BamHI fragments. Although the endogenous sheep beta-lactoglobulin genes contribute to the hybridisation in these bands, the increased intensity in samples from 6LL225, 6LL231 and 6LL240 indicate that these bands derive primarily from the injected beta-lactoglobulin-Factor IX fusion gene, confirming the integrity of the 3' ends of the construct. HindIII cleaved DNA: lane 1, 12.1 kb purified SalI-XbaI fragment excised from pSS1tgXS-FIX; lanes 2–5 DNA from 6LL225, 6LL231, 6LL239 and 6LL240. The probe was p5'G3'CVI. The hybridising 12.1 kb HindIII fragment (6LL225, 6LL231 and 6LL240), identical in size with the injected fragment indicates a head to tail arrangement; the 15.6 kb fragment common to the same sheep indicates that head to head repeats are also present. These data indicate that in sheep 6LL225, 6LL231 and 6LL240 the SalI-XbaI fragment derived from pSS1tgXS-FIX (the beta-lactoglobulin-Factor IX fusion gene) has integrated without detectable rearrangement in tandem arrays. In sheep 6LL239 the data is compatible with the integration of a single unrearranged copy of this fragment.

EXAMPLE 6

Transmission of Factor IX Sequences to the Next Generation

Figure 5A:
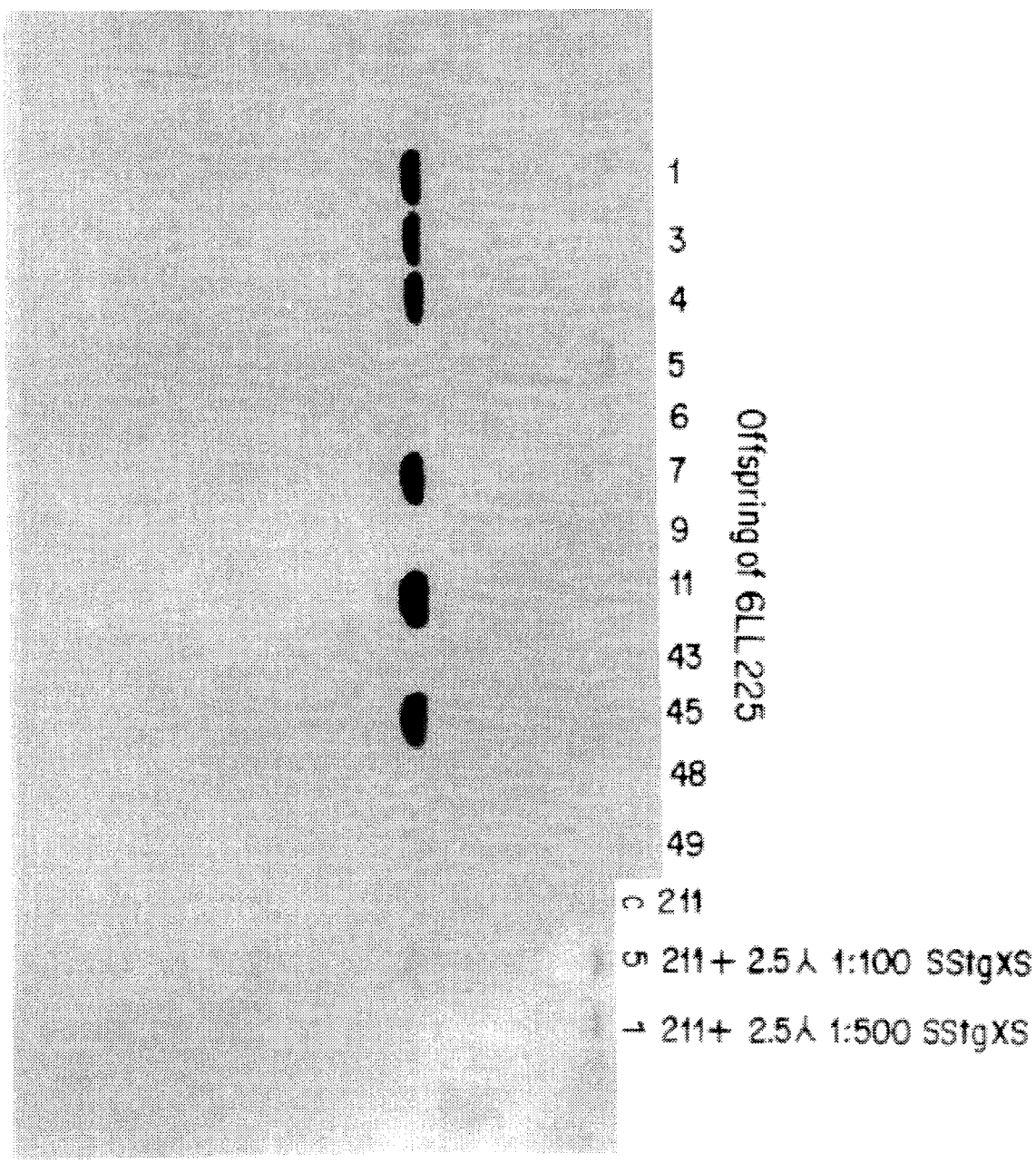
FIG. 5a shows a Southern blot analysis of sheep DNA and illustrates the inheritance of the beta-lactoglobulin fusion gene by the real generation.

The male transgenic sheep 6LL225 from Example 5 (carrying approximately 40 copies of the SalI-XbaI fragment prepared from pSS1tgXS-FIX) was successfully mated to a number of Finn-Dorset and East Friesland ewes. His progeny were analysed by Southern blotting of DNA prepared from blood samples using the human Factor IX plasmid probe p5'G3'CVI, as described. A Southern blot of this analysis on some of his progeny is shown in FIG. 5a. Lanes numbered 1,3,4,5,6,7,9,11,43,45,48 and 49, DNA from progeny of 6LL225 (designated 7R1, 7R3 etc.—7R49), lane c 211, DNA from control (nontransgenic) sheep 6LL211, lanes 5–211 and 1–211, DNA from sheep 6LL211 plus 5 and 1 copy equivalents of pSS1tgXS-FIX. These data show that transgenic sheep 6LL225 has transmitted the Factor IX sequences to 6 out of 12 of his progeny and, therefore that these sequences have been incorporated into the germline.

EXAMPLE 7

Expression of the Gene Encoding Ovine Beta Lactoglobulin in Transgenic Mice

Transgenic mice were generated essentially by the techniques described in Gordon and Ruddle, in Methods in Enzymology Vol 101 (1983), (Eds. Wu, Grossman and Moldave), Academic Press pp411–432. Several transgenic mice carrying the SalI fragment of the clone lambda SS- 1 (FIG. 3) were produced. One of these, B-Lac 7, a female was shown to carry 15–20 copies of the SalI fragment. B-lac 7 was mated a number of times and produced a number of offspring which inherited the SS-I sequences.

Milk was obtained from mice 8–12 days after the birth of a litter. This was accomplished by intra-peritoneal injection of 0.3 IU oxytocin (Sigma) & 7 mcl/g animal of Hypnorm/ Hypnovel (Fleckneil, Vet. Rec. Dec. 10, 1983, p574), after having previously removed the pups for a four hour period, waiting 20 minutes and then massaging the individual mammary gland by hand. Milk was collected in a 50 mcl capillary tube.

Figure 6:
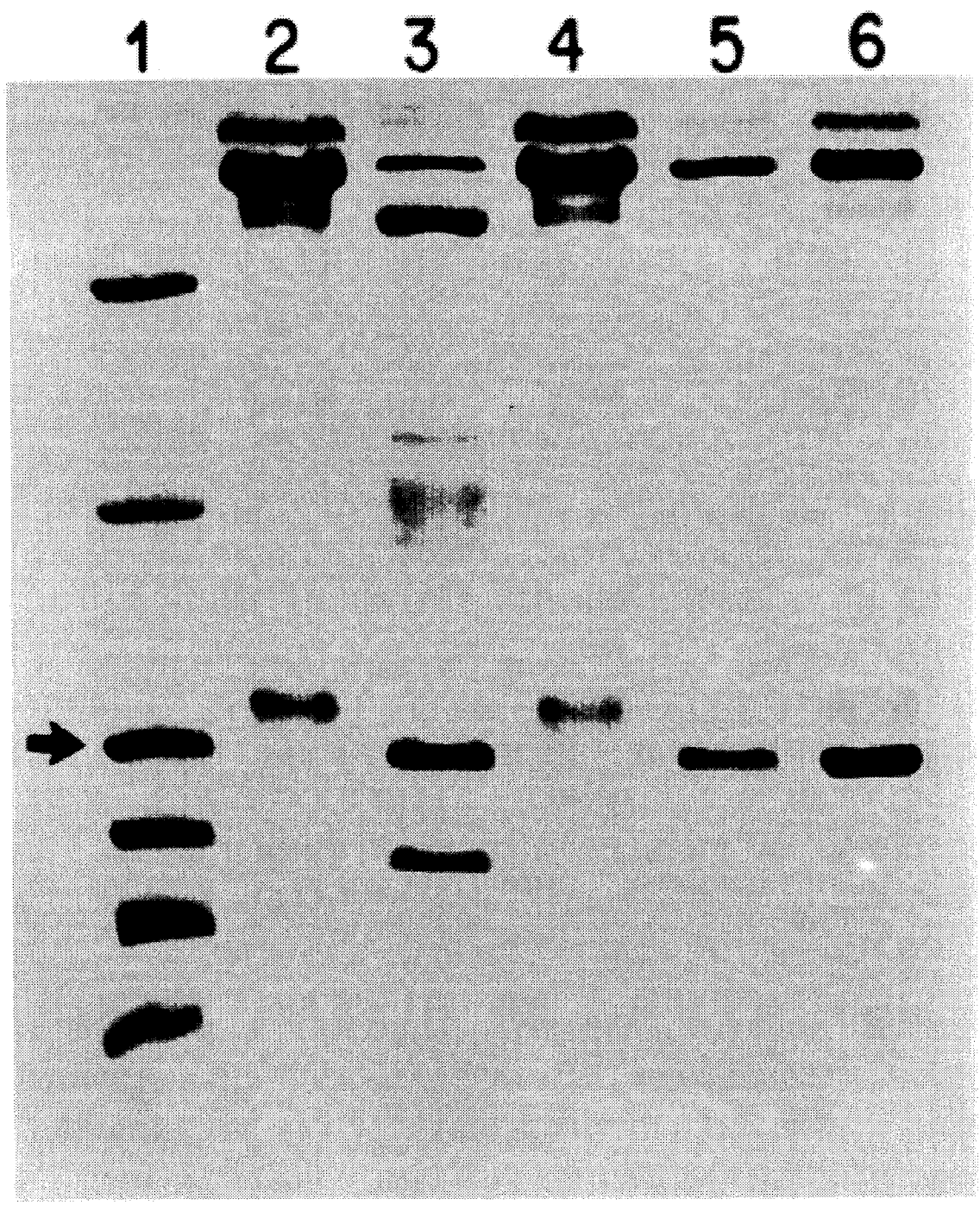
FIG. 6 shows an SDS-PAGE analysis of murine and ovine whey proteins.
Figure 7:
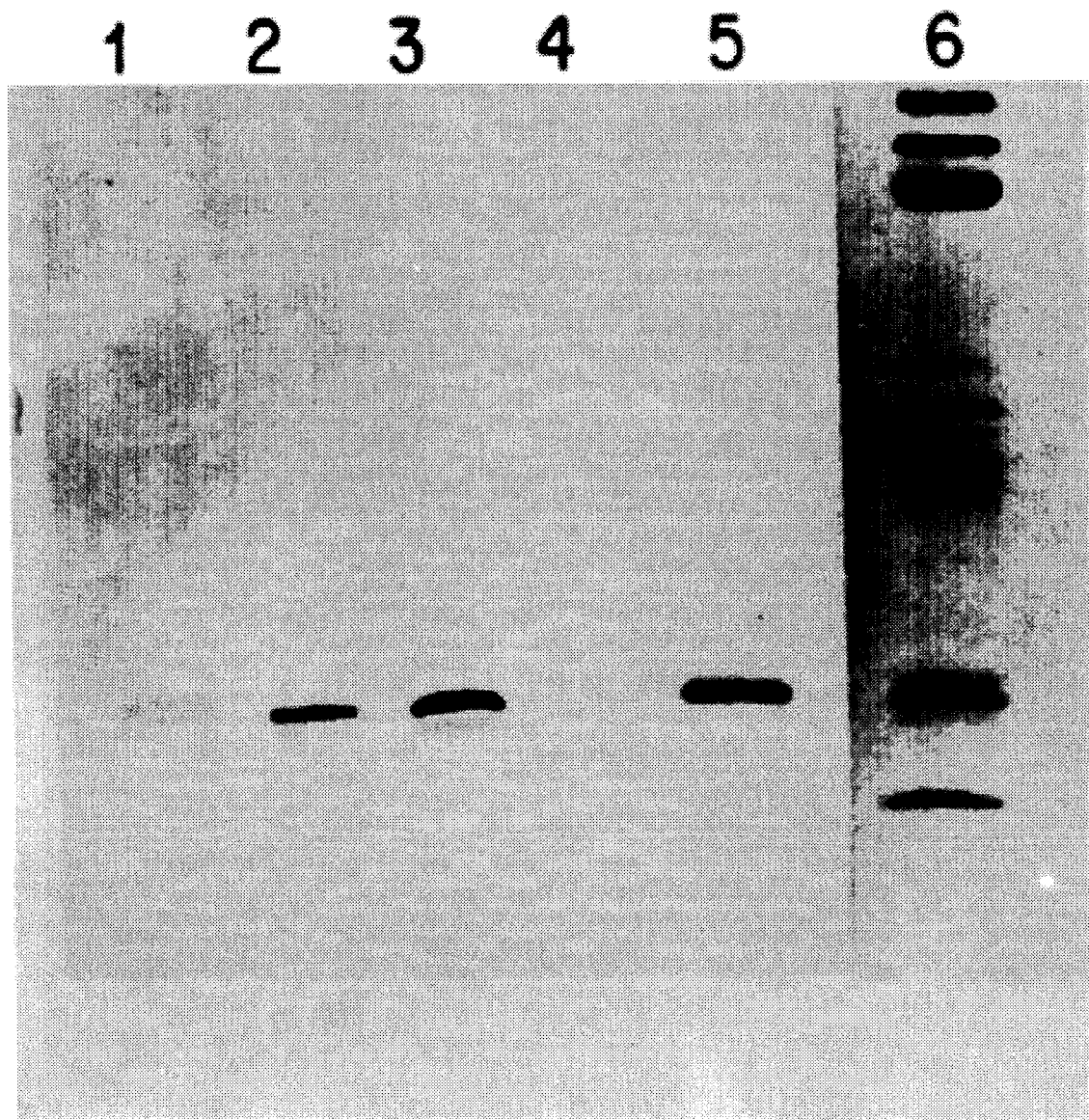
FIG. 7 shows a Western blot analysis of sheep and mouse proteins.

The mouse milk was diluted 1:5 in distilled water, centrifuged briefly in a bench centrifuge to defat and the caseins precipitated by addition of 1 N HCl to a final pH of 4.6. After centrifugation in a bench centrifuge the whey proteins were removed, precipitated with 5% trichloracetic acid and analysed by polyacrylamide gel electrophoresis according to Laemmli (*Nature* 277, 680–684 (1970). (FIG. 6 shows an SDS PAGE Analysis of Murine and Ovine Whey Proteins. Lane 1, marker proteins; 2, normal mouse whey; 3, sheep whey; 4, normal mouse whey; 5, B-lac7 whey; 6, B-lac7 whey (2.5×5). The band corresponding to beta lactoglobulin in the marker track and in ovine whey is arrowed.) Anti-sera raised in rabbits against ovine beta-lactoglobulin was used to detect ovine beta-lactoglobulin by Western blotting (Burnett, Anal. Bioches., 112, 195–203, (1981)) on samples resolved by gel electrophoresis. FIG. 7 shows a Western Blot Analysis. The Western blot was reacted with rabbit anti-beta-lactoglobulin serum and anti-rabbit Ig peroxidase serum. (Lane 1, marker proteins; 2, sheep whey; 3, B-lac7 whey; 4, normal mouse whey; 5, purified beta-lactoglobulin; 6, Coomassie stained sheep whey (run in parallel)).

This analysis showed that large amounts of beta-lactoglobulin were secreted into mouse milk, indicating that SS-1 was being expressed at high levels in B-lac 7. This clone presumably contains all the necessary sequences to ensure high levels of expression in the mammary gland of a transgenic mouse and can thus be expected to function as efficiently, if not more so, in the homologous species i.e. in a transgenic sheep. Consequently, fusion genes derived from this clone can also be expected to express (efficiently) in the ovine mammary gland.

EXAMPLE 8

Expression of Human Factor IX in the Milk of Transgenic Ewes

Two female sheep, 6LL231 and 6LL240 (each carrying approximately 10 copies of SalI-XbaI fragment prepared from pSS1tgXS-FIX) were successfully mated to East Friesland rams. After birth the lambs were allowed to suckle naturally for about two weeks to stimulate lactation. Milk (approximately 25 ml from each animal) was collected by hand into sterile plastic containers. Milk from a control (nontransgenic) lactating ewe was also collected. The samples were frozen at −20° C. and delivered to the Scottish National Blood Transfusion Service at the Royal Infirmary, Edinburgh, where radioimmunoassays (RIA's) for human Factor IX were performed.

Figure 8:
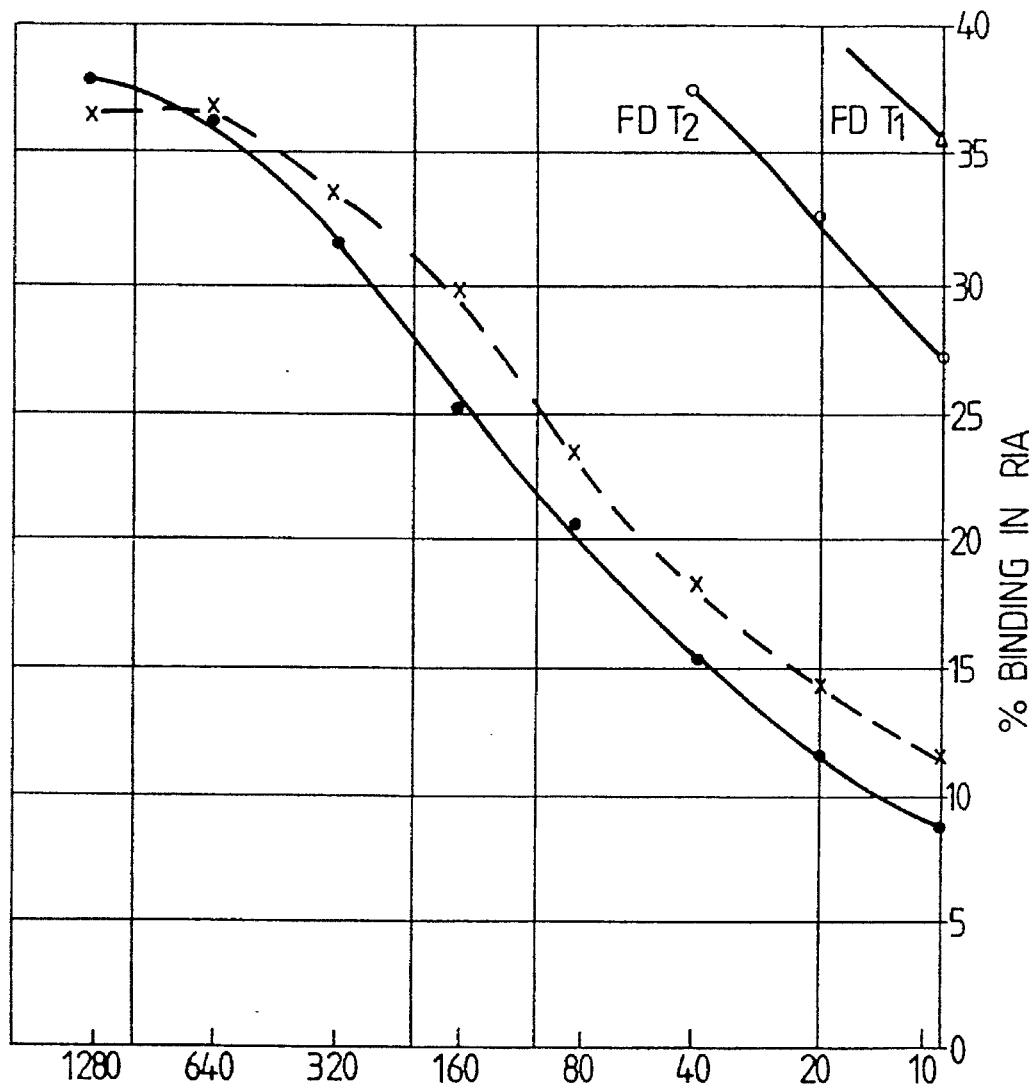
FIG. 8 shows a RIA of milk obtained from transgenic ewe-sheep carrying the beta-lactoglobulin fusion gene as described.

Transgenic and control milk were dialysed against distilled water overnight at 4° C. and then freeze-dried. Freeze-dried sample were resuspended in distilled water and then centrifuged to separate the cream and examined by RIA for the presence of human Factor IX as follows:

A standard curve, using normal human pooled plasma diluted in RIA buffer (50 mM Tris/HCl, 0.25% gelatin, 1% Tween-20, 10 mM HCl, pH 7.2) was established using dilutions of $1/10$–$1/1280$ (see FIG. 8). In order to rule out any interference by milk in the assay, normal pool plasma was similarly diluted in control milk, and a standard curve established. Dilutions of samples of freeze-dried milk from 6LL231 and 6LL240 were assayed. Each tube in the RIA comprised the following: 50 mcl RIA buffer, 50 mcl sample dilution, 50 mcl rabbit polyclonal anti-Factor IX antibody (Dako-Patts), at a $1/30000$ dilution and 50 mcl 1125 labelled Factor IX. A control for maximum binding was set up comprising 100 mcl RIA buffer, 50 mcl antibody and 50 mcl of 1125 Factor IX. A control for non-specific binding was also set up comprising 150 mcl RIA buffer, 50 mcl 1125 trace.

After overnight incubation 50 mcl of Sepharose-S1000 conjugated with donkey anti-rabbit IgG was mixed in the tubes and the beads recovered by sucrose separation. The RIA assay is sensitive to about 0.125 international units (iu)/dl. Any sample containing Factor IX above this level will inhibit maximum binding in the RIA.

The % binding in the RIA was plotted against the reciprocal of the dilution factor for the following samples:
1. Normal pool plasma
2. Normal pool plasma plus milk
3. Freeze dried milk samples from 6LL231 (T1)
4. Freeze dried milk samples from 6LL240 (T2)
These results are shown in FIG. 8.

Milk from both 6LL231 (T1) and 6LL240 (T2) exhibited detectable levels of Factor IX at 2.5 iu/dl and 8.0 iu/dl, respectively. No activity was detected in control milk at the level of sensitivity of the assay. These data show that transgenic ewes carrying the beta-lactoglobulin-factor IX fusion gene (specifically the SalI-XbaI fragment derived from pSS1tgXS-FIX (also generally designated pSS1tgXS-TARG)) express this gene and secrete the human protein into the milk. This establishes a basis for the production of human proteins in this manner.

We claim:

1. A female transgenic sheep whose somatic and germ cells contain a transgene construct, said transgene construct comprising:
   (a) a DNA sequence encoding a polypeptide which does not naturally occur in the milk of a non-transgenic sheep; and
   (b) a β-lactoglobulin promoter operably linked to said DNA sequence encoding said polypeptide;
wherein said transgene construct is integrated in such a way that said DNA sequence encoding said polypeptide is expressed in the mammary gland of said sheep to produce a proteinaceous compound comprising said polypeptide in the milk of said female transgenic sheep.

2. The female transgenic sheep of claim 1, wherein said proteinaceous compound is a blood coagulation factor or a subunit of a blood coagulation factor.

3. The female transgenic sheep of claim 2, wherein said blood coagulation factor is Factor IX.

4. The female transgenic sheep of claim 1, wherein said proteinaceous compound is $\alpha_1$-antitrypsin.

* * * * *

UNITED STATES PATENT AND TRADEMARK OFFICE
CERTIFICATE OF CORRECTION

PATENT NO. : 5,476,995

DATED : December 19, 1995

INVENTOR(S) : Clark et al.

It is certified that error appears in the above-indentified patent and that said Letters Patent is hereby corrected as shown below:

At column 5, line 5, "micelies" is incorrect and should be replaced with -- micelles --. At column 5, lines 13-33, Table 2 is incorrect and should be replaced with:

-- TABLE 2

Protein composition of Various Milks

| g/litre | Bovine | Ovine | Murine | Human |
|---|---|---|---|---|
| CASEINS | | | 7 | |
| Alpha S1 | 10 | 12 | | ) |
| Alpha S2 | 3.4 | 3.8 | | ) 0.4 |
| Beta | 10 | 16 | | 3 |
| Kappa | 3.9 | 4.6 | | 1 |
| MAJOR WHEY PROTEINS | | | | |
| Alpha lactalbumin | 1 | 0.8 | trace | 1.6 |
| Beta lactoglobulin | 3 | 2.8 | no | no |
| Whey acidic protein | no | no | 2 | no |
| OTHER WHEY PROTEINS | | | | |
| Serum albumin | 0.4 | • | • | 0.4 |
| Lysozyme | trace | • | • | 0.4 |
| Lactoferrin | 0.1 | • | • | 1.4 |
| Immunoglobulins | 0.7 | • | • | 1.4 |

(Data compiled from various sources) -- .

UNITED STATES PATENT AND TRADEMARK OFFICE
CERTIFICATE OF CORRECTION

PATENT NO. : 5,476,995

DATED : December 19, 1995

INVENTOR(S) : Clark et al.

It is certified that error appears in the above-indentified patent and that said Letters Patent is hereby corrected as shown below:

At column 6, line 21, "micelies" is incorrect and should be replaced with -- micelles --.
At column 20, line 44 (Claim 1, line 11), insert -- female transgenic -- between "said" and "sheep"; and at line 46 (Claim 1, line 13), delete "female transgenic".

At column 12, line 39, "-ysis" is incorrect and should be replaced with -- lysis --.

Signed and Sealed this

Eighth Day of October, 1996

*Attest:*

BRUCE LEHMAN

*Attesting Officer*  *Commissioner of Patents and Trademarks*